United States Patent [19]

Sullivan, Jr.

[11] Patent Number: 4,934,352
[45] Date of Patent: Jun. 19, 1990

[54] SURGICAL RETRACTOR HANDLE CONSTRUCTION

[76] Inventor: Eugene M. Sullivan, Jr., 8741 Backcreek Rd., Boston, N.Y. 14025

[21] Appl. No.: 669,743

[22] Filed: Nov. 7, 1984

Related U.S. Application Data

[63] Continuation-in-part of Ser. No. 436,040, Oct. 22, 1982, abandoned.

[51] Int. Cl.⁵ .............................................. A61B 17/02
[52] U.S. Cl. ........................................................ 128/20
[58] Field of Search ................................ 128/20, 341; 16/DIG. 12, DIG. 24, DIG. 25; 74/548, 551.9

[56] References Cited

U.S. PATENT DOCUMENTS

| | | | |
|---|---|---|---|
| 579,277 | 3/1897 | Lord et al. | 74/551.9 |
| 1,388,911 | 8/1921 | Allmund | 74/548 |
| 1,708,578 | 4/1979 | Hyde | 128/20 |
| 1,891,658 | 12/1932 | Thomas | 74/548 |
| 2,863,444 | 12/1958 | Winsten | 128/20 |
| 3,196,865 | 7/1965 | Rose | 128/20 |
| 3,463,144 | 8/1969 | Hammond | 128/20 |
| 3,750,652 | 8/1973 | Sherwin | 128/20 |
| 3,857,386 | 12/1974 | Ashbell | 128/20 |
| 3,888,117 | 6/1975 | Lewis | 128/20 |
| 3,998,217 | 12/1976 | Trumbull et al. | 128/20 |
| 4,052,980 | 10/1977 | Grams et al. | 128/18 |
| 4,116,232 | 9/1978 | Rabban | 128/20 |
| 4,151,838 | 5/1979 | Crew | 128/20 |
| 4,226,228 | 10/1980 | Shin et al. | 128/20 |
| 4,461,284 | 7/1984 | Fackler | 128/20 |
| 4,481,947 | 11/1984 | Chester | 128/20 |

FOREIGN PATENT DOCUMENTS

| | | | |
|---|---|---|---|
| 73010 | 3/1892 | Fed. Rep. of Germany | 74/551.9 |
| 13856 | 6/1904 | Norway | 128/20 |
| 708 | of 1913 | United Kingdom | 74/551.9 |

OTHER PUBLICATIONS

Francis Mitchell-Heggs and H. Guy Radcliffe Drew, The Instruments of Surgery, (date of publication unknown), pp. 59-71.
The Kny-Scheerer Company, Surgical Instruments, (date of publication unknown), p. 5173.
The Kny-Scherer Company Catalog, *Illustrations of Surgical Instruments*, 1902, p. 5152.
Charles Lentz & Sons Catalog, Surgical Instruments, Hospital Supplies, 1911, pp. 46 and 47.

*Primary Examiner*—Max Hindenburg
*Attorney, Agent, or Firm*—Bernard, Rothwell & Brown

[57] ABSTRACT

A surgical retractor designed to retract large areas in abdominal cavity surgery. The retractor is comprised of a handle that may be used interchangeably with different sized retractor blades to suit a particular surgical purpose. The handle is disposed or can be adjusted to be disposed at an angle of generally 90° with respect to the retractor blade to afford an easier and more comfortable hold and pull than that experienced with any other designed retractor. The retractor may be fitted with one large retractor blade where previously two or three small retractors were used, and is, therefore, useful in small hospitals in major surgery such as aneurysms, Whipples and node dissections.

24 Claims, 2 Drawing Sheets

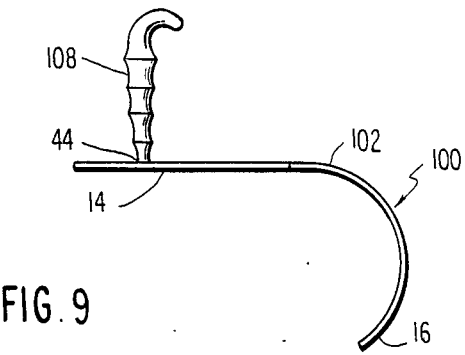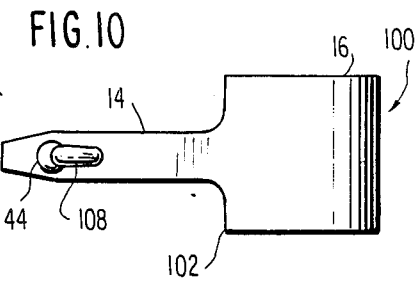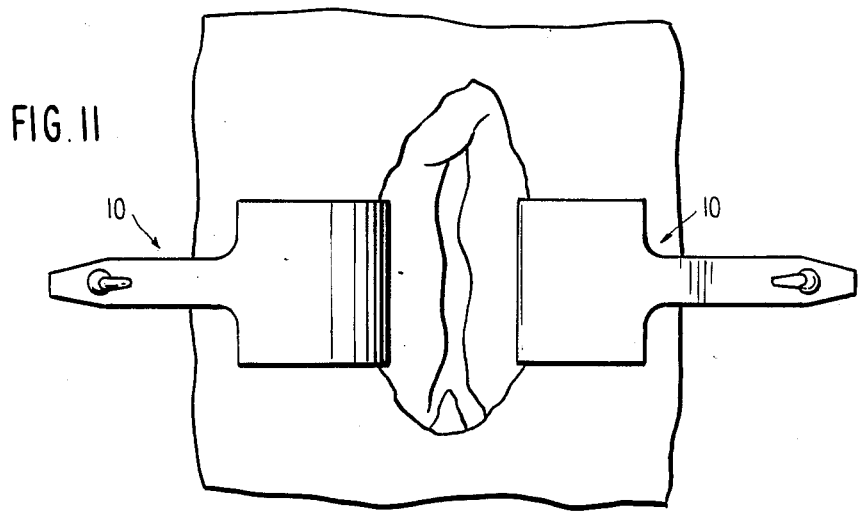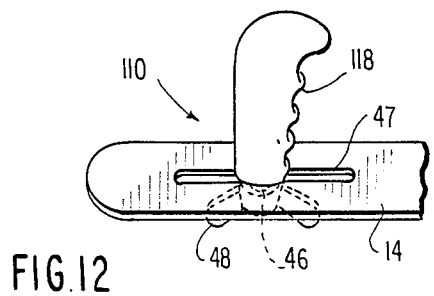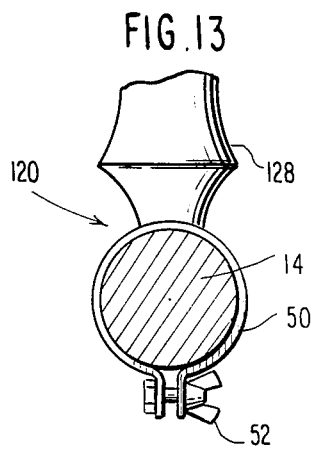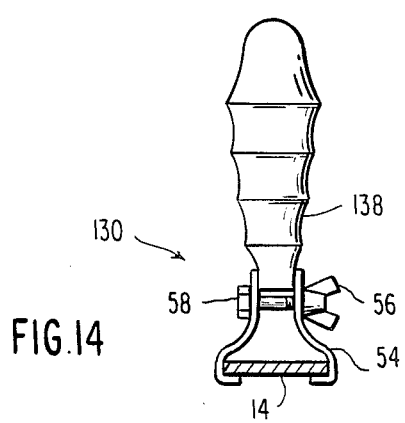

SURGICAL RETRACTOR HANDLE CONSTRUCTION

This is a continuation-in-part of application Ser. No. 436,040 filed Oct. 22, 1982 now abandoned.

BACKGROUND OF THE INVENTION

1. Field of the Invention

The present invention relates to the design of surgical retractors used to retract large areas in the abdominal cavity during surgery.

2. Description of the Prior Art

Previous surgical retractors such as the standard Deaver and Richardson retractors are generally small in size and require two to three hands to provide sufficient operative exposure during a surgical procedure. Also, the handle of these retractors is in line with the retractor blade with the result that a surgeon's assistant performing the retraction will experience great fatigue of the arm during the long periods of time required for certain types of surgery.

Attempts to overcome the disadvantages inherent in the Deaver and Richardson retractors were generally embodied in the self-retaining retractors such as those of U.S. Pat. No. 3,463,144 and U.S. Pat. No. 3,998,217. However, oftentimes it is difficult to find all the parts and sometimes it is cumbersome to set up these types of retractors, particularly in emergency situations.

SUMMARY OF THE INVENTION

This invention provides a surgical retractor which will allow an individual assistant surgeon or second assistant to be able to retract tissue for a long period of time in a comfortable manner. This invention provides a surgical retractor with a handle at a right angle to the retractor blade or a variation thereof so that one can apply traction to the retractor in a comfortable manner with the hand in a grasp position (such as shaking hands) with the elbow at 90°. This manner of retraction utilizes one's shoulder and arm muscles rather than using the wrist and forearm muscles with attendant greater leverage and less fatigue.

This invention overcomes the disadvantages of the prior art devices by providing a surgical retractor with an adjustable handle which allows a surgeon's assistant to set the angle of the handle to suit his anatomical make-up and minimize the fatigue of his own arm, resulting in a smoother and more efficient surgical technique. The surgical retractor of this invention may also be designed with an attachable and detachable handle that can be attached to wide or narrow retractor blades and a variety of other instruments. By designing large retractors such as 5", 7" and 9" blades, combined with the use of this type of handle, one assistant with one hand is able to retract large amounts of tissue with very little fatigue, thus providing good operative exposure during a surgical procedure.

The retractor is designed to be used in a large surgical procedure such as aneurysms, Whipples and node dissection with the use of minimal personnel for retraction. This is especially important in small community hospitals where there is not the surplus of help available as in university centers.

BRIEF DESCRIPTION OF THE DRAWING

In the accompanying diagram:

FIG. 9 is a side elevation view of the surgical retractor of FIG. 8;

FIG. 10 is a top view of the surgical retractor of FIG. 8;

FIG. 11 is a plan view of a pair of surgical retractors being used in accordance with the invention;

FIG. 12 is a partial perspective view of a modified handle for a surgical retractor in accordance with this invention;

FIG. 13 is an elevation view of a modified portion of a handle for a surgical retractor in accordance with this invention;

FIG. 14 is an elevational view of another modified handle on a surgical retractor in accordance with the invention.

FIG. 15 is a perspective view of still another variation of a surgical retractor in accordance with the invention;

FIG. 16 is an elevational view of a still further variation of a surgical retractor in accordance with the invention;

FIG. 17 is a plan view of a retractor and a handle mounting member detachably fastened to a surgical retractor blade in accordance with the invention;

FIG. 18 is an elevational view of a removable handle which can be fastened to the attachment member of FIG. 17;

FIG. 19 is an elevational view of the attachment member and retractor blade of FIG. 17;

FIG. 20 is a plan view of the handle attachment member of FIGS. 17 and 19 attached at a sideways extending angle;

FIG. 21 is a plan view of another variation of an attachment member for detachably securing a retractor blade in accordance with the invention;

FIG. 22 is an elevational view of an attachment member of FIG. 21;

FIG. 23 is an elevational view of another variation of a detachable handle for the blocks of FIGS. 17, 19, 21 and 22; and FIG. 24 is an elevational view of still another variation of a detachable handle for the attachment members of FIGS. 17, 19, 21 and 22.

DESCRIPTION OF THE PREFERRED EMBODIMENTS

Figure 1:
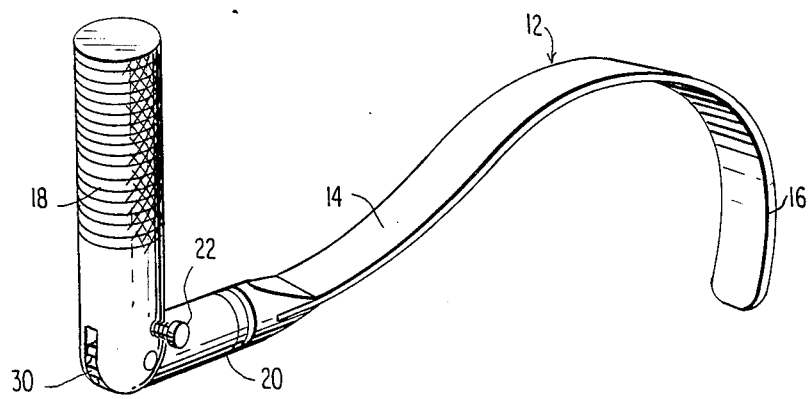
FIG. 1 is a perspective view of a surgical retractor in accordance with this invention.

As shown in FIG. 1, one embodiment of the invention is a surgical retractor including a retractor blade 12 having a straight portion 14 and a curved portion 16, and a handle 18 releasably attached by connector 20 on the blade 12. The handle 18 is disposed generally at a 90° angle with respect to the retractor blade 12 and straight portion thereof 14. This orientation will provide a comfortable grip to most users of the retractor.

Figure 4:
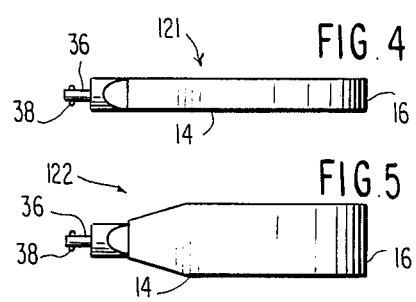
FIG. 4 is a top plan view of a second variation of the surgical retractor blade which may be used with the handle of FIGS. 1 and 2.
Figure 6:
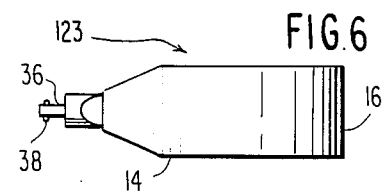
FIG. 6 is a top plan view of a fourth variation of the surgical retractor which may be used with the handle of FIGS. 1 and 2.
Figure 7:
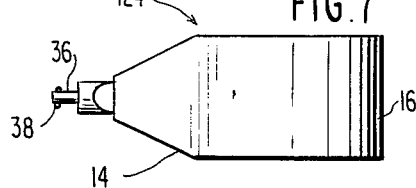
FIG. 7 is a top plan view of a fifth variation of the surgical retractor which may be used with the handle of FIGS. 1 and 2.

The retractor blade 12 is formed from a surgical stainless steel strip having a thickness of about 0.625 inch (1.59 mm), a width of about 1 inch (2.54 mm) and a length of about 12 inches (30 cm). The end portion 16 is formed into a circular arc having a radius of curvature of about 3 inches (7 cm) extending for an arc of about 150°. A blade variation 121 in FIG. 4 is about 1 inch (2.5 cm) shorter while variations 122, 123 and 124 in FIGS. 5, 6 and 7 have widths of about 2, 3 and 4 inches (5, 7.5 and 10 cm), respectively. Even wider variations of 5, 7 and 9 inches (13, 18 and 23 cm) are preferred for some operating procedures. Generally the arc of the curved portion 16 must be greater than 90° in order to properly engage and hold the tissue during retraction. The length of the blade and the radius of the curvature may vary depending upon the particular operating circumstances and tissue involved. Wider blades are preferred for most extensive major operations in order to avoid using two or more narrow retractors in place of the larger retractor to pull back the same tissue.

Figure 2:
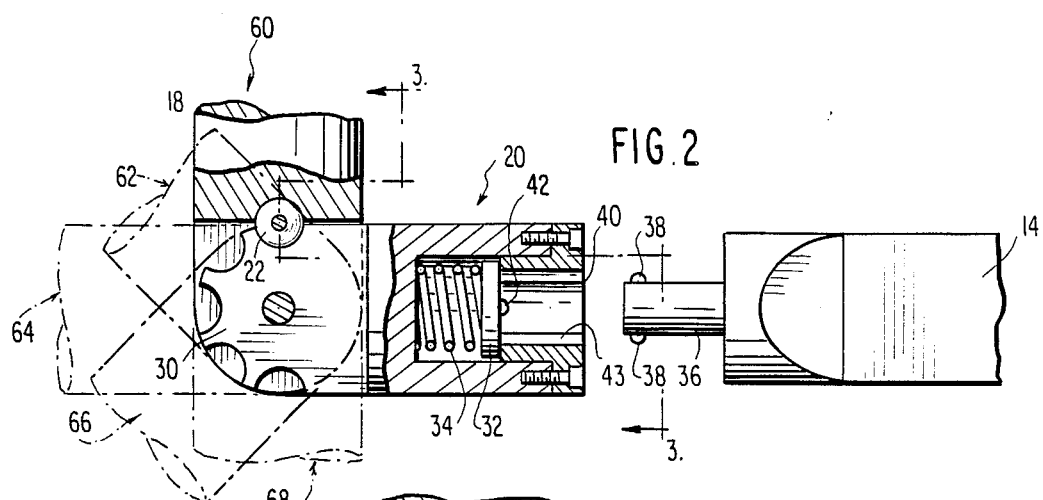
FIG. 2 is a side elevation view, partially in section, of a handle, retractor and bayonet connector portion broken away from the retractor of FIG. 1 with handle disconnected from the blade.
Figure 3:
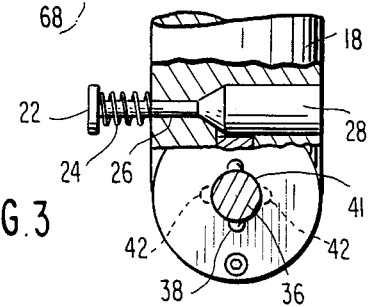
FIG. 3 is a section view taken along line 3—3 of FIG. 2.

Conveniently the handle 18 is detachable so that it may be used with a variety of blades such as blades 121, 122, 123 and 124. The connector 20, as shown in FIGS. 2 and 3, is a bayonet-type connector which has a male portion shaft 36 mounted on the end of the straight portion 14 with nubs 38 projecting from the distal portion thereof. The handle includes a mating female portion with a member 40 having a bore 41 with grooves 43 for receiving the shaft 36 and nubs 38. A disc 32 is biased by compression spring 34 behind the member 40 for retaining the nubs 38 within notches 42 formed in the rear of the member 40. The connector 20 is designed so that the shaft 36 with the nubs 38 oriented as shown in FIG. 2 can be inserted in the bore 41 with the nubs 38 sliding in the grooves 43 until the disc 32 is depressed and the retractor blade 12 rotated to engage the nubs 38 in the notches 42 where the bias of the disc 32 and spring 34 tend to retain the retractor blade against rotation.

The handle 18 is in the form of a cylinder of suitable size for being conveniently grasped by a user. Knurling is provided for aiding the gripping.

For some individuals' anatomical make-up and some surgical procedures it may be desirable that the handle 18 be disposed at a somewhat different angle of orientation with respect to the retractor blade 12 and straight portion 14 thereof. As shown in FIG. 2 and as indicated in dashed lines at 60, 62, 64, 66 and 68, the handle 18 of this invention may be set in five different angles with respect to the blade 12 and the straight portion thereof 14. To accomplish this, the lower portion of the handle 18 has a slot therein into which is received a sectored gear-like member of the connector portion upon which the remaining portion of the handle 18 is pivotably mounted. A push button 22 biased by a compression spring 24 is connected by a shaft to a locking lug 28 slidably mounted in a bore in the upper handle portion for selectively engaging into circumferentially spaced recesses in the gear sector member. The handle 18 may be unlocked and adjusted to any of the five angles of orientation by depressing the button 22 and rotating the upper portion of the handle to the desired position. As shown in FIG. 2, these five angles are (1) 90° upward, (2) 45° upward and outward, (3) horizontally outward, (4) 45° downward and outward, and (5) 90° downward relative to the horizontal plane of the straight portion 14 of the retractor blade.

Figure 8:
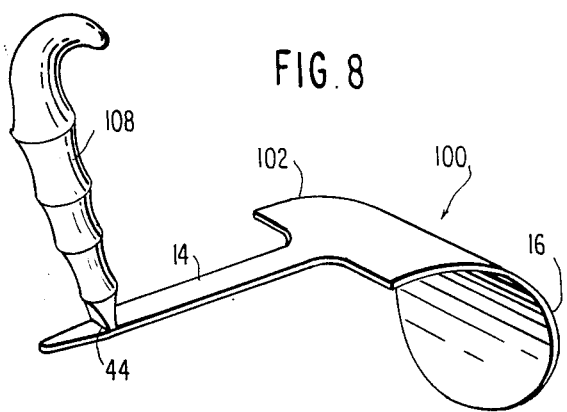
FIG. 8 is a perspective view of another variation of a surgical retractor in accordance with this invention.

As shown in FIG. 8, a second embodiment of the surgical retractor of this invention is generally indicated at 100. The surgical retractor 100 is comprised of a retractor blade 102 having a straight portion 14 and a curved portion 16, a handle 108 and a weld joint 44. A handlebar grip is disposed on the handle 108 to provide a handle of a length and size that will permit all the fingers of the hand to easily extend around the handle when grasped. The handle 108 of this embodiment of the surgical retractor is permanently fixed to the retractor blade 102 by the weld joint 44; therefore, in this embodiment the handle 108 is not interchangeable with different sized retractor blades. However, the handle 108 is disposed generally at an angle of 95° with respect to the straight portion 14 resulting in a much more comfortable pull than that experienced with conventional Deaver or Richardson retractors.

A third embodiment of the surgical retractor of this invention is generally indicated at 110 in FIG. 12. In this embodiment a handle 118 is attached to the straight portion 14 of the retractor blade 12 by a ratchet connector 46 and a wing nut 48. A handlebar grip is disposed on the handle 118 to provide a handle of a length and size that will permit all the fingers of the hand to easily extend around the handle when grasped. The handle 118 is adjustable longitudinally with respect to the straight portion 14 by loosening the wing nut 48 disposed on the ratchet connector 46 and moving the handle to the desired position in the track 47. When the desired position is reached, the wing nut is tightened on the handle by turning it counterclockwise until the handle is secured.

In a fourth embodiment of this invention, generally indicated at 120 in FIG. 13, a handle 128 is attached is to the straight portion 14 with the use of a ligature connector 50 and a set screw 52. A handlebar grip is disposed on the handle 128 to provide a handle of a length and size that will permit all the fingers of the hand to easily extend around the handle when grasped. The ligature connector 50 is attached directly to the handle 128 and consists of a metal strip that will encircle the straight portion 14. In this embodiment the handle 128 may be adjusted longitudinally with respect to the straight portion 14 by loosening the set screw 52 and adjusting the handle 128 with attached ligature connector to the desired position on the straight portion 14. When the desired position is reached, the set screw 52 is tightened to lock the handle 128 with attached ligature connector into the desired position. The handle 128 with attached ligature connector 50 of this embodiment may be interchanged at will with different sized retractor blades to suit a particular purpose.

In a fifth embodiment of this invention, generally indicated at 130 in FIG. 14, a handle 138 is attached to the straight portion 14 with the use of a clip connector 54, a wing nut 56 and a set screw 58. A handlebar grip is disposed on the handle 138 to provide a handle of a length and size that will permit all the fingers of the hand to easily extend around the handle when grasped. The clip connector 54 is permanently attached to the handle 138 and is designed to grasp either side of the straight portion 14. The handle 138 of this embodiment may be adjusted longitudinally with respect to the straight portion 14 by loosening the wing nut 56 and adjusting the handle 138 to the desired orientation with respect to the straight portion 14. When the desired position is reached, the handle 138 may be locked into place on the straight portion 14 by tightening the wing nut 56 on the set screw 58 by turning the wing nut 56 in a clockwise direction.

In a sixth embodiment shown in FIG. 15, a handle unit indicated generally at 202 is provided for releasably attaching to the straight portion 14 of a retractor blade 204 which can be a retractor of the type commonly employed in surgical procedures. The handle unit 202 includes an elongated block 206 having the left portion thereof bifurcated by a slot 208 for receiving the distal end of the straight portion 14 of the retractor 204. The slot 208 extends from the left end of the block 206 past the mid-point of the block generally equi-distance between the upper and lower surfaces of the block 206 to form upper and lower clamping portions. The block 206 is wider than the distal portion of the retractor in the slot 208 so that the upper and lower clamping portions extend on the opposite sides of the distal retractor portion. Screws 210 and 212 have heads recessed in the upper clamping portion and shank portions threaded into the lower clamping portion on opposite sides of the distal retractor portion for forcing the upper and lower clamping portions tightly against the distal retractor portion in the slot 208. Set screws 214 and 216 are threaded in the upper clamping portion over the distal retractor portion for engaging the upper surface of the distal retractor portion to further secure the handle unit 202 to the retractor. The unit 202 also includes handle 220 mounted to the right portion of the block 206 and extending upwardly therefrom. The handle 220 can be formed at an oblique angle to the block 206, as shown, or can extend upwardly at 90° relative to the block 206. Conveniently the handle 220 is formed with finger recesses 222 for enabling the handle 220 to be comfortably gripped.

The unit 202 can be either designed for a single use after which it is discarded or can be constructed of materials suitable for being cleaned and re-sterilized so that it may be reused. The unit 202 may be made by molding a plastic or synthetic resin, or by machining and welding a metal such as aluminum or stainless steel. The handle unit 202 has the advantage that it can be used on retractors presently used in surgical procedures without substantial modification of the existing retractors; this replacement of existing retractors is not required. Such retractors generally have straight handle portions which can be received in the slot 208 and secured by clamping therein. It is noted that the width of the curved portion 16 of the retractor 204 can be made wide similar to the embodiments shown in FIGS. 5, 6 and 7.

In a variation shown in FIG. 16, a detachable handle 230 is in the form of a cylinder. A slot 232 is cut perpendicular to the axis of the handle 230 near to but spaced from the lower end of the handle for receiving the distal end of the straight portion 14 of the retractor blade 204. A threaded bore is formed in the bottom end of the handle 230 for receiving a set screw 234 for securely clamping the distal end of the retractor in the slot 232 to releasably fasten the handle 230 on the retractor blade 204. The cylindrical surface of the handle 230 is knurled to improve the gripping thereof.

Another variation of the detachable handle is illustrated in FIGS. 17, 18 and 19 and employs a block-like attachment member 240 with a slot or recess 242 formed in the left end thereof for receiving the distal end portion of the straight portion 14 of a retractor blade 244. The set screws 214 and 216 threaded in the member 240 above the slot 242 secure the attachment member 240 on the retractor blade 244. The member 240 has finger recesses 246 for enabling the attachment member 240 to be gripped by hand to operate the retractor. Additionally the block 240 is formed with a threaded bore 248 for receiving the threaded end 250 of a handle 252 so as to extend upward form the attachment member 240. The handle 246 conveniently is in the form of a cylinder with its cylindrical surface knurled for readily being gripped by a surgical assistant. The detachable handle unit of FIGS. 17, 18 and 19 has the advantage that it can be employed in two manners, namely, with or without the handle 252 secured in the attachment member 240. Additionally as shown in FIG. 20 the attachment member 240 can be attached at many other positions on the handle 14, such as the illustrated position extending sideways at a 90° angle.

Figure 5:
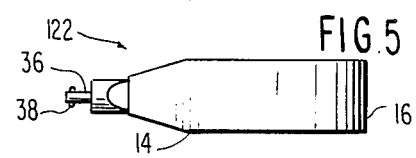
FIG. 5 is a top plan view of a third variation of the surgical retractor which may be used with the handle of FIGS. 1 and 2.

Another attachment member variation 260, illustrated in FIGS. 21 and 22 is similar to the unit 206 in FIG. 5 in that member 260 includes side clamping screws 210 and 212, and is similar to the unit of FIGS. 17 and 19 in that it can be used with the removable handle 252, FIG. 18.

Detachable handle variations 270 and 272, shown in FIGS. 23 and 24, can be utilized in place of the detachable handle 252 of FIG. 18 for the attachment members of FIGS. 17, 19, 21 and 22. The handle variation 270 has the cylindrical handle portion formed at an angle such that when the handle 270 is securely threaded in the attachment portions 240 or 260 of FIGS. 19 and 22, handle 270 will extend with the orientation as illustrated in FIG. 23 to enable easy and comfortable pulling over a prolonged period of time. The T-shaped handle 272 of FIG. 24 is designed so that the upper horizontal member 274 will extend perpendicular to the longitudinal direction of the attachment members 240 and 260 when secured tightly in the threaded bore 248 to enable comfortable gripping of the handle over a prolonged period of time. Alternatively, the handles 252 270 and 272 may employ conventional attachment means other than the threaded ends 250 with corresponding substitution of a mating attachment bore or recess 248.

Since many variations, modifications and changes in detail may be made to the above-described embodiments without departing from the scope and spirit of the invention, it is intended that all matter in the foregoing description and in the accompanying drawings be interpreted as only illustrative and not limiting on the invention as defined in the following claims.

I claim:
1. A surgical retractor comprising:
    (a) an elongated strip-like retractor blade having at one end thereof a substantially straight portion which is substantially parallel with a direction of manual pulling force applied to the blade during surgical retraction of tissue, the blade further having a tissue-engaging curved portion at its other end, said curved portion extending from said straight portion in a substantially circular arc of greater than 90° so as to engage tissue to be retracted by manual pulling force applied in a direction substantially parallel to the straight portion;

(b) a handle having a cylindrical configuration and having a size and shape designed to be easily gripped by all fingers of a hand; and (c) means for connecting the handle to the straight portion such that the handle extends perpendicularly from the straight portion at an angle of about 90° relative thereto such that the handle extends perpendicular to the direction of manual pulling force applied during surgical retraction of tissue to substantially reduce fatigue over extended periods of employment.

2. The surgical retractor of claim 1 wherein the handle is adapted such that the handle may be adjusted to extend from the straight portion at at least one additional angle with respect to the straight portion other than 90° to minus 90°.

3. The surgical retractor of claim 2 wherein said means for connecting said handle to said straight portion includes means for releasably connecting the handle to the blade.

4. The surgical retractor of claim 1 wherein said means for connecting said handle to said straight portion includes means for releasably connecting the handle to the blade.

5. The surgical retractor of claim 1 wherein said means for connecting said handle to said straight portion comprises a weld joint.

6. The surgical retractor of claim 5 wherein said handle has a handlebar grip.

7. The surgical retractor of claim 1 wherein said means for connecting said handle to said straight portion comprises a ratchet connector.

8. The surgical retractor of claim 7 wherein said handle is adjustable longitudinally with respect to said straight portion and said handle connecting means includes screw means.

9. The surgical retractor of claim 7 wherein said handle has a handlebar grip.

10. The surgical retractor of claim 8 wherein said handle has a handlebar grip.

11. The surgical retractor of claim 1 wherein said means for connecting said handle to said straight portion comprises a ligature connector.

12. The surgical retractor or claim 11 wherein said handle has a handlebar grip.

13. The surgical retractor of claim 1 wherein said means for connecting said handle to said straight portion comprises a clip connector.

14. The surgical retractor of claim 13 wherein a wing nut and set screw is disposed on said handle such that the handle may be anchored on said straight portion by tightening said wing nut.

15. The surgical retractor of claim 1 wherein the curved portion of the retractor blade extends on a first side from the straight portion, and the handle extends on a side opposite to the first side from the straight portion.

16. A surgical retractor comprising:

(a) an elongated strip-like retractor blade having at one end thereof a substantial straight portion which is substantially parallel with a direction of manual pulling force applied to the blade during surgical retraction, the blade further having a tissue-engaging curved portion at its other end, said curved portion extending downwardly from said straight portion when the straight portion is horizontally oriented, the curved portion extending in a substantially circular arc of greater than 90° so as to engage tissue to be retracted by manual pulling force in a direction parallel to the straight portion;

(b) an attachment member having a horizontal slot for receiving the one end of the retractor blade and releasable means for securely gripping the one end of the retractor blade in the slot to fasten the attachment member to the retractor blade; and (c) a handle extending upwardly from the attachment member, the handle having a size and shape to be easily gripped by all fingers of a hand, the handle extending upwardly with respect to the downwardly extending curved portion to enable prolonged pulling of the retractor during surgical retraction with minimum fatigue.

17. A surgical retractor as claimed in claim 16 further including means for releasably mounting the handle on the attachment member, and wherein the attachment member includes means for enabling easy manual gripping thereof when the handle is removed.

18. A surgical retractor as claimed in claim 17 wherein the handle is T-shaped.

19. A surgical retractor as claimed in claim 16 wherein the releasable means includes set screw means threaded in the attachment member for engaging the retractor blade in the slot to fasten the attachment member to the retractor blade.

20. A surgical retractor as claimed in claim 19 wherein the handle extends at an angle of generally 90° relative to the straight portion of the retractor blade.

21. A surgical retractor as claimed in claim 16 wherein the slot bifurcates a portion of the attachment member to form upper and lower clamping members, and the releasable means includes screw means for forcing the upper and lower clamping members toward each other to grip the straight portion of the retractor blade therebetween.

22. A surgical retractor comprising:

(a) a retractor connecting portion extending in a direction substantially parallel with a direction of manual pulling force applied to the retractor during surgical retraction of tissue;

(b) a tissue-engaging curved portion extending from one end of the retractor connecting portion, the curved portion extending downwardly from the retractor connecting portion when the retractor connecting portion is horizontally oriented, the curved portion extending in a substantially circular arc of greater than 90° for engaging tissue to be retracted by manual pulling force applied in a direction substantially parallel to the retractor connecting portion; and (c) a handle extending upwardly from another end of the retractor connecting portion, the handle having a size and shape to be easily gripped by all fingers of a hand, the handle extending upwardly with respect to the downwardly extending curved portion to enable prolonged pulling of the retractor during surgical retraction with minimum fatigue.

23. A surgical retractor comprising:

(a) a retractor connecting portion extending in a direction substantially parallel with a direction of manual pulling force applied to the retractor during surgical retraction of tissue;

(b) a tissue-engaging curved portion extending from one end of the retractor connecting portion, the curved portion extending downwardly from the retractor connecting portion when the retractor connecting portion is horizontally oriented, the curved portion extending in a substantially circular arc of greater than 90° for engaging tissue to be retracted by manual pulling force applied in a direction substantially parallel to the retractor connecting portion; and (c) a handle extending downwardly from another end of the retractor connecting portion, the handle having a size and shape to be easily gripped by all fingers of a hand, the handle extending downwardly with respect to the downwardly extending curved portion to enable prolonged pulling of the retractor during surgical retraction with minimum fatigue.

24. A surgical retractor comprising:
(a) a retractor connecting portion extending in a direction of manual pulling force applied to the retractor during surgical retraction of tissue;

(b) a tissue-engaging curved portion extending from one end of the retractor connecting portion, the curved portion extending downwardly from the retractor connecting portion when the retractor connecting portion is horizontally oriented, the curved portion extending in a substantially circular arc of greater than 90° for engaging tissue to be retracted by manual pulling force applied in a direction substantially parallel to the retractor connecting portion; and (c) a handle extending perpendicularly from another end of the retractor connecting portion at an angle of about 90° relative to the retractor connecting portion and to the direction of manual pulling force applied during retraction of tissue, the handle having a size and shape to be easily gripped by all fingers of a hand, the handle enabling prolonged pulling of the retractor during surgical retraction with minimum fatigue.

* * * * *